US009920472B2

(12) United States Patent  
Yamanaka et al.

(10) Patent No.: US 9,920,472 B2  
(45) Date of Patent: Mar. 20, 2018

(54) FLAME RETARDANT SYNTHETIC LEATHER

(71) Applicants: TEIJIN LIMITED, Osaka (JP); MARUBISHI OIL CHEMICAL CO., LTD., Osaka (JP)

(72) Inventors: Katsuhiro Yamanaka, Tokyo (JP); Tsuyoshi Takeda, Tokyo (JP); Kuniaki Kondo, Osaka (JP); Masaki Haruyoshi, Osaka (JP)

(73) Assignee: TEIJIN LIMITED, Osaka (JP)

( * ) Notice: Subject to any disclaimer, the term of this patent is extended or adjusted under 35 U.S.C. 154(b) by 672 days.

(21) Appl. No.: 14/405,519

(22) PCT Filed: Jun. 7, 2013

(86) PCT No.: PCT/JP2013/066412  
§ 371 (c)(1),  
(2) Date: Dec. 4, 2014

(87) PCT Pub. No.: WO2013/187492  
PCT Pub. Date: Dec. 19, 2013

(65) Prior Publication Data  
US 2015/0132607 A1 May 14, 2015

(30) Foreign Application Priority Data

Jun. 11, 2012 (JP) .................................. 2012-131646

(51) Int. Cl.
| | |
|---|---|
| *D06N 3/00* | (2006.01) |
| *C07F 9/6571* | (2006.01) |
| *C08K 5/5357* | (2006.01) |
| *C09K 21/12* | (2006.01) |
| *C14C 9/00* | (2006.01) |

(52) U.S. Cl.  
CPC ..... *D06N 3/0059* (2013.01); *C07F 9/657163* (2013.01); *C07F 9/657181* (2013.01); *C08K 5/5357* (2013.01); *C09K 21/12* (2013.01); *C14C 9/00* (2013.01); *D06N 2211/28* (2013.01)

(58) Field of Classification Search  
CPC .............. D06N 3/0059; D06N 2211/28; C07F 9/657163; C07F 9/657181; C08K 5/5357; C09K 21/12; C14C 9/00  
USPC ........................................................ 428/540  
See application file for complete search history.

(56) References Cited

U.S. PATENT DOCUMENTS

| | | |
|---|---|---|
| 3,141,032 A | 7/1964 | Friedman |
| 4,154,721 A | 5/1979 | Valdiserri et al. |
| 4,178,281 A | 12/1979 | Horn, Jr. |
| 4,257,931 A | 3/1981 | Granzow |
| 2004/0127611 A1 | 7/2004 | Yamanaka et al. |
| 2011/0092623 A1 | 4/2011 | Yamanaka et al. |

FOREIGN PATENT DOCUMENTS

| | | |
|---|---|---|
| CN | 1781976 | 6/2006 |
| CN | 101021045 | 8/2007 |
| EP | 2 832 924 | 2/2015 |
| GB | 1 515 223 | 6/1978 |
| JP | 52-12329 | 1/1977 |
| JP | 53-39698 | 4/1978 |
| JP | 54-157156 | 12/1979 |
| JP | 1-260072 | 10/1989 |
| JP | 52-12329 | * 1/1997 |
| JP | 2003-213109 | * 7/2003 |
| JP | 2003-306679 | 10/2003 |
| JP | 2004-18585 | 1/2004 |
| JP | 2004-18586 | 1/2004 |
| JP | 2004-131580 | * 4/2004 |
| JP | 2004-169197 | * 6/2004 |
| JP | 2005-15942 | 1/2005 |
| JP | 2009-19304 | 1/2009 |
| JP | 2009-507976 | 2/2009 |

(Continued)

OTHER PUBLICATIONS

International Search Report dated Jul. 9, 2013 in International (PCT) Application No. PCT/JP2013/066412.

(Continued)

*Primary Examiner* — Leszek Kiliman  
(74) *Attorney, Agent, or Firm* — Wenderoth, Lind & Ponack, L.L.P.

(57) ABSTRACT

Flame retardant synthetic leather having high flame retardancy and excellent physical properties (light resistance, heat resistance and feeling).

The flame retardant synthetic leather contains an organic phosphorus compound (component A) represented by the following formula (1).

$$\begin{array}{c}X^1\diagdown\underset{O-CH_2}{\overset{O}{\underset{\|}{P}}}\diagdown\underset{CH_2-O}{\overset{O-CH_2}{\underset{}{C}}}\diagdown\underset{O}{\overset{O}{\underset{\|}{P}}}\diagup X^2\end{array} \quad (1)$$

(In the formula, $X^1$ and $X^2$ are the same or different and each an aromatic substituted alkyl group represented by the following formula (2).)

$$-(AL)-(Ar)_n \quad (2)$$

(In the formula, AL is a branched or linear aliphatic hydrocarbon group having 1 to 5 carbon atoms, and Ar is a phenyl group, naphthyl group or anthryl group, all of which may have a substituent. "n" is an integer of 1 to 3, and Ar may be bonded to any carbon atom contained in AL.)

5 Claims, No Drawings

(56) References Cited

FOREIGN PATENT DOCUMENTS

| JP | 2009-209489 | | 9/2009 |
|----|-------------|---|--------|
| JP | 2009-235628 | * | 10/2009 |
| JP | 2010-77554 | * | 4/2010 |
| WO | 2004/060900 | | 7/2004 |
| WO | 2007/031450 | | 3/2007 |
| WO | 2009/145341 | | 12/2009 |

OTHER PUBLICATIONS

Office Action issued Aug. 12, 2015 in corresponding Japanese Application No. 2014-521415.
Office Action dated Aug. 18, 2015 in corresponding Chinese patent application No. 201380030360.
English translation of the International Preliminary Report on Patentability and Written Opinion dated Dec. 24, 2014 in PCT/JP2013/066412.
European Search Report dated Dec. 3, 2015 in corresponding European patent Application No. 13 80 3496.

* cited by examiner

FLAME RETARDANT SYNTHETIC LEATHER

TECHNICAL FIELD

The present invention relates to synthetic leather having high flame retardancy and excellent physical properties.

BACKGROUND ART

Synthetic leather has been used in a wide variety of fields such as interior materials for automobiles and railways, and interior materials for buildings and furniture as a substitute for natural leather. Synthetic leather used as an interior material for vehicles such as automobiles or a cover material for furniture is desired to have soft feeling, flexibility, mechanical strength and durability. Since it is easily burnt, it needs to be flame retardant. For example, there are FMVSS-302 and JIS-D-1201 for interior materials for automobiles, a 45° ethyl alcohol method, which is a non-metal material testing method for rail cars, for interior materials for railways, and JIS-A-1321 for wall covering materials. High flame retardancy which meets these standards is required.

Synthetic leather is formed by laminating a surface resin layer of polyurethane, polyolefin or polyvinyl chloride on a fiber substrate such as a woven, knitted or nonwoven fabric. An adhesive layer may be existent between the fiber substrate and the surface resin layer.

As for the flame retardation of synthetic leather, a method for flame retarding at least one of the fiber substrate, the surface resin layer and the adhesive layer is reported, and a halogen-based compound or a combination of a halogen-based compound and antimony oxide is effective as a flame retardant in use. However, in recent years, flame retardation without using a halogen-based flame retardant has been desired from the viewpoint of environmental conservation and a harmful effect of a gas generated at the time of combustion. As the non-halogen-based flame retardant, there are known a large number of flame retardants such as ammonium phosphate, ammonium sulfamate, ammonium sulfate, borax, boric acid, ammonium hydroxide, magnesium hydroxide and phosphoric acid esters (Patent Documents 1 to 4).

However, when a water-soluble flame retardant is added in an amount required for the production of a flame retarding effect, there occur problems such as the thickening of a synthetic resin emulsion or solution, destruction (gum-up), the deterioration of the strength of a resin film, heat resistance and feeling. Since ammonium polyphosphate which contains no halogen and has a flame retarding effect relatively has water solubility, it elutes into water and causes problems with the physical properties and flame retardancy of a product under the condition that water resistance is required. Further, even ammonium polyphosphate which is capsulated with an improved resin is not satisfactory in terms of water resistance. Therefore, synthetic leather which has satisfactory flame retardancy and physical properties by using a phosphorus-based flame retardant and not a halogen-based flame retardant is not provided yet.

(Patent Document 1) JP-A 01-260072
(Patent Document 2) JP-A 2005-015942
(Patent Document 3) JP-A 2009-019304
(Patent Document 4) JP-A 2009-209489

DISCLOSURE OF THE INVENTION

It is an object of the present invention to provide flame retardant synthetic leather which has high flame retardancy and excellent physical properties (light resistance, heat resistance and feeling).

The inventors of the present invention conducted intensive studies to solve the above problems and found that an organic phosphorus compound (component A) represented by the following formula (1) which is insoluble or hardly soluble in water has high flame retardancy and excellent physical properties (light resistance, heat resistance, feeling) as a flame retardant for synthetic leather.

That is, the present invention is flame retardant synthetic leather containing the organic phosphorus compound (component A) represented by the following formula (1).

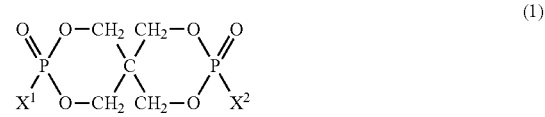

(In the above formula, $X^1$ and $X^2$ are the same or different and each an aromatic substituted alkyl group represented by the following formula (2).)

(In the above formula, AL is a branched or linear aliphatic hydrocarbon group having 1 to 5 carbon atoms, and Ar is a phenyl group, naphthyl group or anthryl group, all of which may have a substituent. "n" is an integer of 1 to 3, and Ar may be bonded to any carbon atom contained in AL.)

The present invention, includes a method of using the organic phosphorus compound (component A) represented by the formula (1) as a flame retardant for synthetic leather. The present invention also includes a method of improving the flame retardancy of synthetic leather, wherein the organic phosphorus compound (component A) represented, by the formula (1) is contained in synthetic leather.

BEST MODE FOR CARRYING OUT THE INVENTION

A detailed description of the flame retardant synthetic leather of the present invention is given below.

[Organic Phosphorus Compound (Component A)]

In the present invention, the organic, phosphorus compound (component A) is a compound represented by the following formula (1).

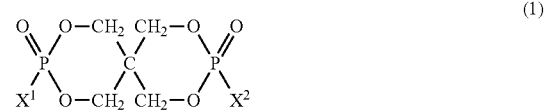

(In the above formula, $X^1$ and $X^2$ are the same or different and each an aromatic substituted alkyl group represented by the following formula (2).)

In the above formula, AL is a branched or linear aliphatic hydrocarbon group having 1 to 5 carbon atoms. The aliphatic hydrocarbon group is selected from alkanediyl groups, alkanetriyl groups and alkanetetrayl groups.

Specific examples thereof include alkylene groups having 1 to 5 carbon atoms such as methylene group, ethylene group, trimethylene group, isopropyldiyl group, butylene group and pentylene group. Alkanetriyl groups having 1 to 5 carbon atoms such as methanetriyl group, ethanetriyl group, propanetriyl group, butanetriyl group and pentanetriyl group are included. Alkanetetrayl groups having 1 to 5 carbon atoms such as methanetetrayl group, ethanetetrayl group, propanetetrayl group, butanetetrayl group and pentanetetrayl group are also included.

Ar is a phenyl group, naphthyl group or anthryl group, all of which may have a substituent. Examples of the substituent include alkyl groups having 1 to 5 carbon atoms such as methyl group, ethyl group and propyl group, and halogen atoms such as fluorine atom, chlorine atom and bromine atom.

Ar may be bonded to any carbon atom contained in AL. "n" is an integer of 1 to 3.

A compound represented by the following formula (3) is preferred as the organic phosphorus compound (component A).

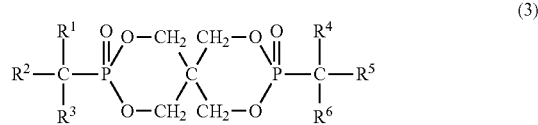

(3)

In the above formula, $R^2$ and $R^5$ may be the same or different and each a phenyl group, naphthyl group or anthryl group, all of which may have a substituent. Examples of the substituent include alkyl groups having 1 to 5 carbon atoms such as methyl group, ethyl group and propyl group, and halogen atoms such as fluorine atom, chlorine atom and bromine atom.

$R^1$, $R^3$, $R^4$ and $R^6$ may be the same or different and each a substituent selected from hydrogen atom, branched or linear alkyl group having 1 to 4 carbon atoms, and phenyl group, naphthyl group and anthryl group, all of which may have a substituent. Examples of the alkyl group having 1 to 4 carbon atoms include methyl group, ethyl group, propyl group, isopropyl group, butyl group and t-butyl group. The substituent of the phenyl group, naphthyl group or anthryl group is an alkyl group having 1 to 5 carbon atoms such as methyl group, ethyl group or propyl group, or a halogen atom such as fluorine atom, chlorine atom or bromine atom.

An organic phosphorus compound represented by the following formula (4) is more preferred.

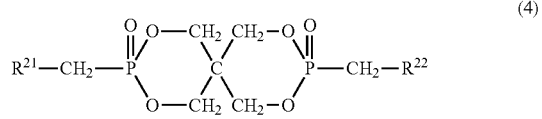

(4)

In the above formula, $R^{21}$ and $R^{22}$ are the same or different and each a phenyl group, naphthyl group or anthryl group, all of which may have a substituent on the aromatic ring, out of which a phenyl group is preferred.

The hydrogen atom of the aromatic ring of the phenyl group, naphthyl group or anthryl group represented by $R^{21}$ and $R^{22}$ may be substituted, and the substituent is methyl, ethyl, propyl, butyl or aryl group having 6 to 14 carbon atoms whose aromatic ring has a bonding group through an oxygen atom, sulfur atom or aliphatic hydrocarbon group having 1 to 4 carbon atoms.

The organic phosphorus compound (component A) represented by the above formula (1) exhibits an extremely excellent flame retarding effect, while it retains water resistance as a flame retardant for synthetic leather. As far as the inventors of the present invention know, it has been extremely difficult to achieve both water resistance and flame retardancy at the same time by using a non-halogen flame retardant for synthetic leather, and there have been a large number of problems to be solved for practical use.

However, according to the present invention, surprisingly, the above organic phosphorus compound (component A) easily achieves both water resistance and a high, level of flame retardancy at the same time and can provide excellent flame retardant synthetic leather as a flame retardant for synthetic leather.

The content of the organic phosphorus compound (component A) is preferably 1 to 300 parts by weight, more preferably 5 to 200 parts by weight, much more preferably 10 to 100 parts by weight based on 100 parts by weight of synthetic leather.

In the present invention, it is possible to use a flame retardant other than the component A and/or other additives in order to reduce the content of the component A and improve the flame retardancy, physical properties and chemical properties of synthetic leather or for another purpose, besides the component A. These components will be described in detail hereinafter.

Although the organic phosphorus compound (component A) as a flame retardant for synthetic leather of the present invention is represented by the above formula (1), the most, preferred typical compound is represented by the following formula (1-a).

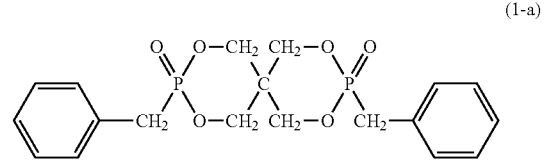

(1-a)

Since the organic phosphorus compound (component A) represented by the above formula (1) has much lower water solubility than that of ammonium polyphosphate which is generally used as a non-halogen-based flame retardant or that of capsulated ammonium polyphosphate, it can provide water-resistant flame retardancy. The solubility in 80° C. hot water of the organic phosphorus compound of the formula (1-a) is not more than 0.5%, that of ammonium polyphosphate is 80.8%, and that of silica-coated ammonium polyphosphate is 12.8%.

A description is subsequently given of a process for synthesizing the organic phosphorus compound (component A) of the present invention. The component A may be produced by a process other than the process which will be described hereinbelow.

The component A is obtained, for example, by reacting phosphorus trichloride with pentaerythritol, treating the oxidized reaction product with an alkali metal compound such as sodium methoxide, and reacting the treated product with aralkyl halide.

The component A may also be obtained by reacting aralkyl phosphonic acid dichloride with pentaerythritol, or by reacting aralkyl alcohol with a compound obtained by reacting phosphorus trichloride with pentaerythritol and then carrying out Arbuzov rearrangement. The latter reaction is described in U.S. Pat. No. 3,141,032, JP-A 54-157156 and JP-A 53-39698.

A specific process for synthesizing the component A will be described hereinbelow, and this process is only for explanation. The component A used in the present invention may be synthesized not only by this process but also by its modified or other processes. A more specific synthesizing process will be explained in Preparation Example which will be described hereinafter.

(I) Organic Phosphorus Compound (1-a) Contained in Component A;

The organic phosphorus compound (1-a) can be obtained by reacting phosphorus trichloride with pentaerythritol, oxidizing the reaction product with tertiary butanol, treating the oxidized reaction product with sodium methoxide and reacting the reaction product with benzyl bromide.

Alternatively, it can be obtained, by reacting phosphorus trichloride with pentaerythritol and heating a reaction product between the obtained product and benzyl alcohol in the presence of a catalyst.

The above-described component. A has an acid value of not more than 0.7 mgKOH/g, preferably not more than 0.5 mgKOH/g. By using the component A having an acid value within this range, flame retardant synthetic leather which is excellent in flame retardancy, hue and heat stability is obtained. The component A having, an acid value of not more than 0.4 mgKOH/g is most preferred. The acid value means the amount (rag) of KOH required for the neutralization of an acid component contained in 1 g of a sample (component A).

Further, the component A has an HPLC purity of preferably at least 90%, more preferably at least 95%. The component A having this purity is preferred as it is excellent in the flame retardancy, hue and heat stability of synthetic leather. The HPLC purity of the component A can be measured effectively by using the following method.

The Develosil ODS-7 having a length of 300 mm and a diameter of 4 mm of Nomura Chemical Co., Ltd, was used as a column, and the column temperature was 40° C. A mixed solution of acetonitrile and water in a volume ratio of 6:4 was used as a solvent, and 5 µl of the solution was injected. A UV-260 nm detector was used.

Although the method of removing impurities contained in the component A is not particularly limited, a method in which repulp cleaning with a solvent such as water or methanol (cleaning with a solvent and filtering are repeated several times) is carried out is the most effective and economically advantageous.

Further, the average particle diameter of the component A is preferably 5 to 100 µm, more preferably 10 to 50 µm.

[Synthetic Leather]

In general, synthetic leather comprises at least a fiber substrate and a surface resin layer. As desired, it may have an adhesive layer for bonding the fiber substrate to the surface resin layer.

In the present invention, the synthetic leather contains the organic phosphorus compound (component A) represented by the formula (1) in at least one of the above substrate and the above layer. That is, preferably, the synthetic leather comprises the fiber substrate and the surface resin layer and contains the organic phosphorus compound (component A) represented by the formula (1) in the fiber substrate and/or the surface resin layer. More preferably, the synthetic leather comprises the fiber substrate, the adhesive layer and the surface resin layer, and contains the organic phosphorus compound (component A) represented by the formula (1) in at least one selected from the group consisting of the fiber substrate, the adhesive layer and the surface resin layer.

(Fiber Substrate)

As the fiber substrate, a woven fabric, knitted fabric or nonwoven fabric is used. As for the type of the fiber material, synthetic fibers such as polyester, polyamide, nylon, acrylonitrile and polypropylene, cellulose-based fibers such as rayon, cotton and linen, and animal fibers such as wool, silk and feather are used alone or in a composite state. The fiber substrate may have a raised surface or a protective layer (abrasion-resistant layer).

To contain the organic phosphorus compound (component A) in the fiber substrate, the organic phosphorus compound (component A) may be contained in the fiber substrate, or a film thereof may be formed on the fiber substrate.

To form the film on the fiber substrate, the organic phosphorus compound (component A) is preferably mixed or dispersed into a dispersant such as water, an organic solvent, a resin solution, resin emulsion or latex to prepare a flame retardant. A surfactant, a stabilizer or another flame retardant may be used as required. As for the mixing ratio, the amount of the organic phosphorus compound (component A) is preferably 5 to 300 parts by weight, more preferably 10 to 200 parts by weight, particularly preferably 20 to 100 parts by weight based on 100 parts by weight of the dispersant. When the amount of the organic phosphorus compound (component A), falls within the above range, a satisfactory flame retarding effect is obtained, and the resin film can be formed well with the result that the quality of the synthetic leather becomes high.

The obtained flame retardant is adhered to the fiber substrate to flame retard the fiber substrate. Although the flame retarding method is not particularly limited, immersion, spraying, brushing or coating with a knife coater which has been employed in the prior art is generally used.

The content of the organic phosphorus compound (component A) in the fiber substrate is preferably 1 to 300 parts by weight, more preferably 5 to 200 parts by weight, much more preferably 10 to 100 parts by weight based on 100 parts by weight, of the fiber substrate. When the content of the organic phosphorus compound fails within the above range, the obtained synthetic leather has high flame retardancy and excellent physical properties (light resistance, heat resistance and feeling) advantageously.

(Surface Resin Layer)

Examples of the resin used in the surface resin layer include polyurethanes (polyester-based, polyether-based, polycarbonate-based and lactone-based), polyesters, polyacrylic acid esters, polymethacrylic acid esters, copolymers of an acrylic acid ester and/or methacrylic acid ester and a vinyl-based monomer or olefin-based monomer, polymers and copolymers of an olefin-based monomer and a vinyl-based monomer, mixtures thereof, polyvinyl acetate, ethylene-vinyl chloride copolymer, SBR (styrene butadiene rubber), vinyl-chloride, vinylidene chloride and mixtures of two or more thereof.

The resin used in the surface resin layer is preferably a polycarbonate-based polyurethane from the viewpoint of feeling and durability.

The surface resin layer may have a single-layer structure or multi-layer structure consisting of two or more layers.

When the organic phosphorus compound (component A) is contained in the surface resin layer, the content of the organic phosphorus compound (component A) is preferably 1 to 300 parts by weight, more preferably 5 to 250 parts by weight, much more preferably 10 to 200 parts by weight based on 100 parts by weight of the surface resin layer (solid-content). When the content, of the organic phosphorus compound falls within the above range, the obtained synthetic leather has high flame retardancy and excellent physical properties (light resistance, heat resistance and feeling) advantageously.

The thickness of the surface resin is preferably 10 to 500 µm, more preferably 20 to 300 µm. When the thickness falls within the above range, the feeling of the synthetic leather becomes excellent advantageously.

(Adhesive Layer)

The flame retardant synthetic leather of the present invention preferably has an adhesive layer for bonding the fiber substrate to the surface resin layer.

As the adhesive, ethylene-vinyl acetate copolymer-based emulsion, polyvinyl chloride paste, polyurethane adhesive and epoxy-based adhesive are used. This adhesive may be applied to a cloth surface or a resin sheet surface.

The resin constituting the adhesive layer is preferably a urethane resin. An adhesive obtained by using a urethane resin which is generally used as an adhesive may be used as the urethane resin. As for the type of the adhesive, either an adhesive for wet lamination which bonds the fiber substrate to the surface resin layer without drying a solvent or an adhesive for dry lamination which bonds the fiber substrate to the surface resin layer after the solvent is dried may be used.

The urethane resin may be a polyester-based, polyether-based or polycarbonate-based urethane resin, or a mixture thereof. The urethane resin is, for example, a urethane resin having an average molecular weight, of 10,000 to 40,000 obtained from at least one diol selected from a polymer diol having an average molecular weight, of 500 to 2,500, such as polyester diol, polyether diol, polyester-ether diol, polycaprolactone diol and polycarbonate diol and at least one organic polyisocyanate selected from organic polyisocyanates such as aromatic diisocyanates, aromatic triisocyanates and alicyclic diisocyanates, and commercially available products of a urethane resin solution having a solid content of 40 to 70 wt % may be used as the urethane resin. Polyester-based urethane resins are particularly preferred.

A urethane curing agent and an urethanizing catalyst may be used to lighten a process load and improve the physical properties of synthetic leather.

When the organic phosphorus compound (component A) is contained in the adhesive layer, the content of the organic phosphorus compound (component A) is preferably 1 to 300 parts by weight, more preferably 5 to 250 parts by weight, much more preferably 10 to 200 parts by weight based on 100 parts by weight of the adhesive layer (solid content). When the content of the organic phosphorus compound falls within the above range, the obtained synthetic leather has high flame retardancy and excellent physical properties (light resistance, heat resistance, feeling) advantageously.

The thickness of the adhesive layer is preferably 10 to 500 μm, more preferably 20 to 300 μm. When the thickness falls within the above range, abrasion resistance becomes high and the feeling of the synthetic leather becomes excellent advantageously.

(Another Flame, Retardant, Other Additives)

In the present invention, a flame retardant other than the organic phosphorus compound (component A) (to be referred to as "combination flame retardant" hereinafter) may be used.

Although the combination flame retardant is not particularly limited, examples thereof include inorganic combination flame retardants such as aluminum hydroxide, titanium oxide, zinc oxide, expandable graphite, magnesium hydroxide, calcium carbonate, zinc borate, ammonium polyphosphate and red phosphorus, and organic combination flame retardants such as melamine, melamine polyphosphate, melamine cyanurate and phosphate-based compound. The combination flame, retardants may be used alone or in combination of two or more.

The phosphate-based compounds as the above combination flame retardant include trioctyl phosphate, triphenyl phosphate, tricresyl phosphate, trixylenyl phosphate, cresyl diphenyl phosphate, cresyl di-2,6-xylenyl phosphate, isopropylphenyl phosphate, tert-butylphenyl phosphate, biphenyldiphenyl phosphate, naphthyldiphenyl phosphate, resorcinol bis(diphenylphosphate), resorcinol bis(dixylenylphosphate), bisphenol A bis(diphenylphosphate), tris(chloropropyl)phosphate, tris(dichloropropyl)phosphate and tris(tribromoneopentyl)phosphate.

Out of these combination flame retardants, melamine polyphosphate and melamine cyanurate are particularly preferred.

The amount of the combination flame retardant is preferably 1 to 200 parts by weight, more preferably 3 to 100 parts by weight, much more preferably 5 to 50 parts by weight based on 100 parts by weight of the organic phosphorus compound (component A).

To the flame retardant synthetic leather of the present invention may be added aids such as antifungal/insecticidal agent, antistatic agent, lubricant, light resistance improver, heat resistance improver, ultraviolet absorbent, antioxidant, water repellent, crosslinking agent, plasticizer, colorant, defoaming agent and flame retarding aid, surfactants such as dispersant and penetrant, stabilizers such as thickener, and fillers such as clay, talc, mica, expandable graphite, wollastonite, kaolin, montmorillonite, bentonite, sepiolite, xonotlite and silica as required.

(Production Process of Flame Retardant Synthetic Leather)

The production process of the flame retardant synthetic leather of the present invention is not particularly limited and may be either a wet process or a dry process.

The wet process as used herein is a process in which a surface resin dissolved in a solvent in a predetermined concentration is applied to a fiber substrate, solidified in a coagulating bath containing a poor solvent to make a large number offline communication holes in the resin layer like sponge, rinsed and dried to obtain a product.

The dry process is a direct coating process in which a surface resin layer is formed by applying a surface resin dissolved in a solvent in a predetermined concentration to a fiber substrate by a known coating technique and volatilizing the solvent by a drier to solidify the resin, or a process in which a surface resin layer is formed by applying a surface resin to release paper by a known coating technique and drying it. Examples of the release paper include silicone type release paper and polypropylene type release paper, and release paper having a flat type, enamel type, mat type or embossed type surface may be used. The release paper is not particularly limited. Then, the polyurethane resin-based adhesive is applied to this surface resin layer by a known coating technique, laminated on the fiber substrate by thermocompression bonding and dried to obtain a product.

Stated more specifically, the synthetic leather can be produced by the following process.

A composition comprising a surface resin (for example, polyurethane resin) is applied to the release paper, and heated and aged as required to form a surface resin layer. Then, a composition comprising an adhesive in a hot molten state (for example, hot melt polyurethane) is applied to the surface of the surface resin layer, laminated on the fiber substrate while the prepolymer composition has viscosity, cooled to room temperature and aged to form an adhesive layer. Finally, the release paper is peeled off.

As the surface resin composition, a processing liquid prepared by adding the organic phosphorus compound (component A) to a surface resin emulsion or a surface resin solution, adding a crosslinking agent and a pigment as required to the obtained mixture, and uniformly dispersing them into the mixture is preferably used.

To apply the surface resin composition (processing liquid) to the release paper, conventionally known methods may be employed, and the method is not particularly limited. For example, methods using a reverse roll coater, spray coater, roll coater, gravure coater, kiss roll coater, knife coater, comma coater and T-die coater may be employed. Out of these, coating with a knife coater or a comma coater is preferred because it can form a uniform thin film layer.

As the composition comprising an adhesive, a processing liquid prepared by adding the organic phosphorus compound (component A) to a resin emulsion for the adhesive layer or a resin solution for the adhesive layer, adding a crosslinking agent as required and uniformly dispersing it in the mixture is preferably used. To apply the composition comprising an adhesive (processing liquid) to the surface resin layer, the above conventionally known methods may be employed.
(Use of Synthetic Leather)

The synthetic leather of the present invention is advantageously used as a raw material for car interior products (such as seats, headrests, tonneau covers, sun visors and ceilings), room interior materials, covers materials for bicycle saddles, cover materials for furniture (chairs and sofas) and bags.

The present invention includes a method of using the organic phosphorus compound (component A) represented by the formula (1) as a flame retardant for synthetic leather.

The present invention also includes a method of improving the flame retardancy of synthetic leather, wherein the organic phosphorus compound (component A) represented by the formula (1) is contained in the synthetic leather.

The present invention further includes a method of improving the flame retardancy of synthetic leather, wherein the organic phosphorus compound (component A) represented by the formula (1) is contained in at least one selected from the group consisting of the substrate, adhesive layer and surface resin layer of the synthetic leather.

EXAMPLES

The following examples are provided for the purpose of further illustrating the present invention but are in no way to be taken as limiting the technical scope of the invention. "Parts" and mean "parts by weight" and "wt %", respectively, and evaluations were made by the following methods.
(1) Frame Retardancy 1

Flame retardancy was evaluated in accordance with FMVSS-302. For evaluation, the combustion distance from the gauge line, the time taken to burn this distance from the gauge line and the combustion rate from the gauge line were each measured three times as specified in FMVSS-302. "Nonflammable" means automatic extinction below the gauge line, h sample having a combustion rate higher than 10 cm/min is rejected.
(2) Flame Retardancy 2

The char length was measured by the 45° air mix burner wire net method of the Fire Service Act. A combustion test was carried out by immersing a combustion test specimen in hot water (50±2° C.×30 minutes) and drying it. When the char length is not more than 7 cm at maximum and not more than 5 cm on average, flame retardancy is acceptable.
(3) Light Resistance As for light resistance, the degree of discoloration after 200 hours of exposure to 83° C. was judged by using a fade meter (JIS-L0842, carbon are lighting method; grade determined by judging the degree of discoloration with a JIS discoloration blue scale; as the grade becomes higher, light resistance becomes higher).
(4) Heat Resistance As for heat resistance, the degree of discoloration after 60 minutes of a treatment at 150° C. in a gear oven drier was checked. ○ means that no discoloration is seen and Δ means that discoloration is seen.
(5) Feeling Feeling was judged by touch with the hand.
(6) Acid Value This was measured in accordance with JIS-K-3504.

Preparation Example 1

Preparation of 2,4,8,10-tetraoxa-3,9-diphosphaspiro [5.5]undecane, 3,9-dibenzyl-3,9-dioxide (FR-1)

22.55 g (0.055 mole) of 3,9-dibenzyloxy-2,4,8,10-tetraoxa-3,9-diphosphaspiro [5.5]undecane, 19.01 g (0.11 mole) of benzyl bromide and 33.54 g (0.32 mole) of xylene were charged into a reactor having a stirrer, a thermometer and a condenser, and dry nitrogen was let flow into the reactor under agitation at room, temperature. Then, heating was started with an oil bath to heat the above mixture at a reflux temperature (about 130° C. for 4 hours under agitation.

After the end of heating, the resulting mixture was left to be cooled to room temperature, and 20 ml, of xylene was added and further stirred for another 30 minutes. The precipitated crystal was separated by filtration and washed with 20 mL of xylene twice. The obtained roughly purified product and 40 mL of methanol were injected into a reactor equipped with a condenser and a stirrer to be refluxed for about 2 hours. After the crystal was cooled to room temperature, it was separated by filtration and washed with 20 mL of methanol, and the obtained filtrate was dried at 120° C. and $1.33 \times 10^2$ Pa for 19 hours to obtain a white flaky crystal.

It was confirmed by mass spectral analysis, $^1$H and $^{31}$P nuclear magnetic resonance spectral analysis and elemental analysis that the product was bisbenzyl pentaerythritol diphosphonate. The yield was 20.60 g, the yield rate was 91%, and the $^{31}$PNMR purify was 99%.

The HPLC purity measured by the method described in this text was 99%. The acid value was 0.05 mgKOH/g.

$^1$H-NMR (DMSO-$d_6$, 300 MHz): δ7.2-7.4 (m, 10H), 4.1-4.5 (m, 8H), 3.5 (d, 4H), $^{31}$P-NMR (DMSO-$d_6$, 120 MHz): δ23.1 (S), melting point: 257° C., average particle diameter: 30 μm 2,4,8,10-tetraoxa-3,9-diphosphaspiro[5,5]undecane, 3,9-dibenzyl-3,9-dioxide {phosphorus-based compound of the formula (1-a) (to be referred to as "FR-1" hereinafter)} synthesized in Preparation Example 1 was used as the organic phosphorus compound (component A) used in Examples.

Example 1

A flame retardant was added to the surface resin layer in this example.
<Treatment Liquid 1> (Processing Liquid for Surface Resin Layer)

| | |
|---|---|
| Polycarbonate-based polyurethane resin (solid content of 30%, DMF solvent) | 100 parts |
| MEK | 50 parts |
| Pigment (carbon black) | 12 parts |
| FR-1 (flame retardant) | 20 parts |
| Crosslinking agent | 2 parts |

The processing liquid for the surface, resin layer prepared by the formulation of the treatment liquid 1 was applied to release paper with a doctor knife to a thickness of 0.1 mm (after drying) and heated at 100° C. for 2 minutes in a drier.
<Treatment Liquid 2> (Processing Liquid for Adhesive Layer)

| | |
|---|---|
| Ester-based polyurethane resin (solid content of 50%, DMF solvent) | 100 parts |
| Urethane curing agent | 10 parts |
| Urethane curing catalyst | 1 part |
| Pigment (carbon black) | 5 parts |

Subsequently, the processing liquid for the adhesive layer prepared by the formulation of the treatment liquid 2 was applied to the surface resin layer on the release paper with a doctor knife to a thickness of 0.1 mm (after drying), laminated on a polyester woven fabric (weight: 200 g/m²) and pressed by means of a mangle (4 kg/m²) and the obtained laminate was aged at 60° C. for 21 hours or more to obtain flame retardant synthetic leather.

Comparative Example 1

Synthetic leather was obtained in the same manner as in Example 1 except that a flame retardant was not contained in the surface resin layer.

Comparative Example 2

Synthetic leather was obtained in the same manner as in Example 1 except that 20 parts of decabromodiphenyl ether was used in place of FR-1 as a flame retardant for the surface resin layer.

Comparative Example 3

Synthetic leather was obtained in the same manner as in Example 1 except that 20 parts of trisdichloropropyl phosphate was used in place of FR-1 as a flame retardant for the surface resin layer.
(test results): Flame retardancy (evaluation of flame retardancy 1) is shown in Table 1, and physical properties are shown in Table 2.

TABLE 1

| | Flame retardancy test (FMVSS-302) | | | | | | | | |
|---|---|---|---|---|---|---|---|---|---|
| | n = 1 | | | n = 2 | | | n = 3 | | |
| Sample name | Distance (mm) | Time (sec) | Rate (cm/min) | Distance (mm) | Time (sec) | Rate (cm/min) | Distance (mm) | Time (sec) | Rate (cm/min) |
| Example 1 | 0 | 0 | non-flammable | 0 | 0 | non-flammable | 0 | 0 | non-flammable |
| Comparative Example 1 | 270 | 119 | 13.6 | 270 | 103 | 15.7 | 270 | 132 | 12.3 |
| Comparative Example 2 | 0 | 0 | non-flammable | 0 | 0 | non-flammable | 0 | 0 | non-flammable |
| Comparative Example 3 | 142 | 168 | 5.1 | 162 | 198 | 4.9 | 172 | 173 | 6.0 |

TABLE 2

| Sample name | Light resistance | Heat resistance | Feeling |
|---|---|---|---|
| Example 1 | grades 4 to 5 | ◯ | Good |
| Comparative Example 1 | grades 4 to 5 | ◯ | Good |
| Comparative Example 2 | grade 4 | ◯ | Slightly hard |
| Comparative Example 3 | grades 3 to 4 | Δ | Slightly tucked |

Example 2

A flame retardant was added to the surface resin layer and the adhesive layer in this example.
<Treatment Liquid 3> (Processing Liquid for Surface Resin Layer)

| | |
|---|---|
| Polycarbonate-based polyurethane resin (solid content of 30%, DMF solvent) | 100 parts |
| MEK | 50 parts |
| Pigment (carbon black) | 12 parts |
| FR-1 (flame retardant) | 30 parts |
| Crosslinking agent | 2 parts |

The processing liquid for the surface resin layer prepared by the formulation of the treatment liquid 3 was applied to release paper with a doctor knife to a thickness of 0.1 mm (after drying) and heated at 100° C. for 2 minutes in a drier.
<Treatment Liquid 4> (Processing Liquid for Adhesive Layer)

| | |
|---|---|
| Ester-based polyurethane resin (solid content of 50%, DMF solvent) | 100 parts |
| Urethane curing agent | 10 parts |
| Urethane curing catalyst | 1 part |
| Pigment (carbon black) | 5 parts |
| FR-1 (flame retardant) | 30 parts |

Subsequently, the processing liquid for the adhesive layer prepared by the formulation of the treatment liquid 4 was applied to the surface resin layer on the release paper with a doctor knife to a thickness of 0.1 mm (after drying), laminated on polyester jersey cloth (weight: 150 g/m$^2$) and pressed by means of a mangle (4 kg/m$^2$), and the obtained laminate was aged at 60° C. for 24 hours or more to obtain flame retardant synthetic leather.

Comparative Example 4

Synthetic leather was obtained in the same manner as in Example 2 except that a flame retardant was not contained in the surface resin layer and the adhesive layer.

Comparative Example 5

Synthetic leather was obtained in the same manner as in Example 2 except, that 30 parts of decabromodiphenyl ether was used in place of FR-1 as a flame retardant for the surface resin layer and the adhesive layer.

Comparative Example 6

Synthetic leather was obtained in the same manner as in Example 2 except that 30 parts of ammonium polyphosphate was used in place of FR-1 as a flame retardant for the surface resin layer and the adhesive layer.
(test results): Flame retardancy (evaluation of flame retardancy 2) is shown in Table 3, and physical properties are shown in Table 4.

TABLE 3

| Sample name | 45° air mix burner wire net method of the Fire Service Act Char length | | |
|---|---|---|---|
| | n = 1 | n = 2 | n = 3 |
| Example 2 | 3.8 | 4.2 | 3.9 |
| Comparative Example 4 | ∞ | ∞ | ∞ |
| Comparative Example 5 | 4.0 | 4.1 | 4.2 |
| Comparative Example 6 | ∞ | ∞ | ∞ |

TABLE 4

| | Light resistance | Heat resistance | Feeling |
|---|---|---|---|
| Example 2 | grades 4 to 5 | ○ | Good |
| Comparative Example 4 | grades 4 to 5 | ○ | Good |
| Comparative Example 5 | grades 3 to 4 | ○ | Good |
| Comparative Example 6 | grade 4 | ○ | Slightly hard |

Example 3

A flame retardant was added to a fiber substrate, in this example.
The fiber substrate was first flame retarded. Treatment liquid (flame-retarding processing liquid for fiber substrate): 50 parts of FR-1 (flame retardant) was added to a solution prepared by adding 10 parts of a surfactant (dispersant) and 40 parts of water to 100 parts of an ester-based polyurethane resin (solid content of 50%, water solvent) wider agitation.
A polyester woven fabric (weight: 200 g/m²) was padded with the above processing liquid for the fiber substrate (squeeze rate of 80%), dried at 80° C. for 5 minutes and heated at 150° C. for 1 minute to obtain a flame retarded fiber substrate.
<Treatment Liquid 5> (Processing Liquid for Surface Resin Layer)

| | |
|---|---|
| Polycarbonate-based polyurethane resin (solid content of 30%, DMF solvent) | 100 parts |
| MEK | 50 parts |
| Pigment (carbon black) | 12 parts |
| Crosslinking agent | 2 parts |

The processing liquid for the surface resin layer prepared by the formulation of the treatment liquid 5 was applied to release paper with a doctor knife to a thickness of 0.1 mm (after drying) and heated at 100° C. for 2 minutes in a drier.
<Treatment Liquid 6> (Processing Liquid for Adhesive Layer)

| | |
|---|---|
| Ester-based polyurethane resin (solid content of 50%, DMF solvent) | 100 parts |
| Urethane curing agent | 10 parts |
| Urethane curing catalyst | 1 part |
| Pigment (carbon black) | 5 parts |

Subsequently, the processing liquid for the adhesive layer prepared by the formulation of the treatment liquid 6 was applied to the surface resin layer on the release paper with a doctor knife to a thickness of 0.1 mm (after drying), laminated on the flame retarded fiber substrate and pressed by means of a mangle (4 kg/m²), and the obtained laminate was aged at 60° C. for 24 hours or more to obtain flame retardant synthetic leather.

Comparative Example 7

Synthetic leather was obtained in the same manner as in Example 3 except that a flame retardant was not contained in the fiber substrate.

Comparative Example 8

Synthetic leather was obtained in the same manner as in Example 3 except that 50 parts of decabromodiphenyl ether was used in place of FR-1 as a flame retardant for the fiber substrate.

Comparative Example 9

Synthetic leather was obtained in the same manner as in Example 3 except that 50 parts of trisdichloropropyl phosphate was used in place of FR-1 as a flame retardant for the fiber substrate.
(test results): Flame retardancy (evaluation of flame retardancy 1) is shown in Table 5, and physical properties are shown in Table 6.

TABLE 5

| | Flame retardancy test (FMVSS-302) | | | | | | | | |
|---|---|---|---|---|---|---|---|---|---|
| | n = 1 | | | n = 2 | | | n = 3 | | |
| Sample name | Distance (mm) | Time (sec) | Rate (cm/min) | Distance (mm) | Time (sec) | Rate (cm/min) | Distance (mm) | Time (sec) | Rate (cm/min) |
| Example 3 | 0 | 0 | non-flammable | 0 | 0 | non-flammable | 0 | 0 | non-flammable |
| Comparative Example 7 | 266 | 100 | 16.0 | 256 | 98 | 15.7 | 268 | 92 | 17.5 |
| Comparative Example 8 | 0 | 0 | non-flammable | 0 | 0 | non-flammable | 0 | 0 | non-flammable |
| Comparative Example 9 | 270 | 190 | 8.5 | 270 | 201 | 8.1 | 265 | 189 | 8.4 |

TABLE 6

| Sample name | Light resistance | Heat resistance | Feeling |
|---|---|---|---|
| Example 3 | grades 4 to 5 | ○ | Good |
| Comparative Example 7 | grades 4 to 5 | ○ | Good |
| Comparative Example 8 | grades 4 to 5 | ○ | Slightly hard |
| Comparative Example 9 | grades 4 to 5 | ○ | Good |

Effect of the Invention

According to the present invention, synthetic leather can be flame retarded without using a halogen-based flame retardant. In addition, the flame retardant synthetic leather obtained by the present invention does not deteriorate in light resistance, heat resistance and feeling.

INDUSTRIAL APPLICABILITY

The flame retardant synthetic leather of the present invention is useful as a material for car interior products (such as seats, headrests, tonneau covers, sun visors and ceilings) and furniture (such as chairs and sofas).

The invention claimed is:

1. A flame retardant synthetic leather comprising a fiber substrate, an adhesive layer and a surface resin layer,
   (i) wherein the surface resin layer comprises a polyurethane and has a thickness of 10 to 500 μm, and
   (ii) wherein an organic phosphorus compound of the following formula (1-a), which has an average particle diameter of 5 to 100 μm is contained in at least one selected from the group consisting of the fiber substrate, the adhesive layer and the surface resin layer,

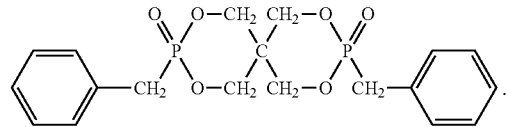

(1-a)

2. The flame retardant synthetic leather according to claim 1, wherein the organic phosphorus compound of the formula (1-a) is contained in an amount of 1 to 300 parts by weight based on 100 parts by weight of the fiber substrate.

3. The flame retardant synthetic leather according to claim 1, wherein the organic phosphorus compound of the formula (1-a) is contained in an amount of 1 to 300 parts by weight based on 100 parts by weight of the surface resin layer.

4. The flame retardant synthetic leather according to claim 1, wherein the organic phosphorus compound of the formula (1-a) is contained in an amount of 1 to 300 parts by weight based on 100 parts by weight of the adhesive layer.

5. The flame retardant synthetic leather according to claim 1, wherein at least one compound selected from the group consisting of aluminum hydroxide, titanium oxide, zinc oxide, expandable graphite, magnesium hydroxide, calcium carbonate, zinc borate, melamine, red phosphorus, ammonium polyphosphate, melamine polyphosphate, melamine cyanurate and phosphoric ester is contained in an amount of 1 to 200 parts by weight based on 100 parts by weight of the organic phosphorus compound of the formula (1-a).

* * * * *